United States Patent
Nadaka et al.

(10) Patent No.: US 6,329,521 B2
(45) Date of Patent: Dec. 11, 2001

(54) PROCESS FOR PREPARING SUBSTITUTED BENZOYL CYANIDE AMIDINOHYDRAZONES

(75) Inventors: Vladimir Nadaka, Lod; Jael Lexmer, Tel Aviv; Joseph Kaspi, Givataim, all of (IL)

(73) Assignee: Chemagis, Ltd., Bnei Brak (IL)

( * ) Notice: Subject to any disclaimer, the term of this patent is extended or adjusted under 35 U.S.C. 154(b) by 0 days.

(21) Appl. No.: 09/789,634

(22) Filed: Feb. 22, 2001

(30) Foreign Application Priority Data

Feb. 25, 2000 (IL) ......................................................... 134730

(51) Int. Cl.⁷ ..................... C07C 255/17; C07C 279/10; C07D 253/075
(52) U.S. Cl. .......................... 544/182; 562/869; 564/230; 564/234
(58) Field of Search ............................ 562/869; 564/230, 564/234; 544/182

(56) References Cited

U.S. PATENT DOCUMENTS

| 3,637,688 | * | 1/1972 | Rees et al. ............................ 544/182 |
| 4,486,354 | * | 12/1984 | Baxter et al. ......................... 544/182 |
| 4,602,017 | * | 7/1986 | Sawyer et al. ........................ 544/182 |
| 4,649,139 | * | 3/1987 | Allan et al. ........................... 544/182 |

FOREIGN PATENT DOCUMENTS

| 0 21 121 | * | 1/1981 | (EP) . |
| 0 142 306 | * | 5/1985 | (EP) . |
| 0 247 892 | * | 5/1987 | (EP) . |

OTHER PUBLICATIONS

Settepani et al.., J. Heterocycl. Chem., 3, 188–190, 1966.*
Rees et al., J. Med. Chem., 15, 859–861, 1972.*

* cited by examiner

Primary Examiner—Mukund J. Shah
Assistant Examiner—Venkataraman Balasubramanian
(74) Attorney, Agent, or Firm—Banner & Witcoff

(57) ABSTRACT

The present invention provides a process for preparing a compound of the general formula (I):

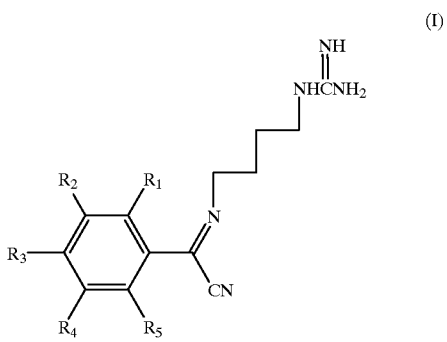

wherein $R_1$ to $R_5$ are independently selected from hydrogen, halogen, $C_{1-6}$ alkyl, $C_{2-6}$ alkenyl, $C_{2-6}$ alkynyl or $C_{1-6}$ alkoxy, all optionally substituted by one or more of halogen, hydroxy and aryl groups, as well as being independently selected from amino, mono- or disubstituted amino, alkenyloxy, acyl, acyloxy, cyano, nitro, aryl and alkylthio groups, which process comprises reacting a compound of the general formula (II):

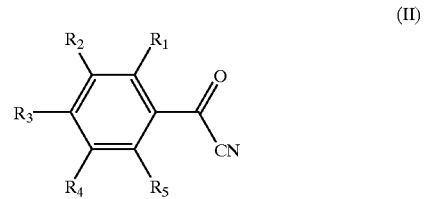

wherein $R_1$ to $R_5$ are as defined in formula (I), with aminoguanidine bicarbonate in a mixture of a water-soluble solvent and polyphosphoric acid.

6 Claims, No Drawings

PROCESS FOR PREPARING SUBSTITUTED BENZOYL CYANIDE AMIDINOHYDRAZONES

FIELD OF THE INVENTION

The present invention relates to a method for preparing substituted benzoyl cyanide amidinohydrazones. More particularly, the present invention pertains to the preparation of these compounds by a reaction of substituted benzoyl cyanides with aminoguanidine in the presence of polyphosphoric acid.

BACKGROUND OF THE INVENTION

It is known that certain 3,5-diamino-6-(substituted phenyl)-1,2,4-triazines are active in the treatment of CNS disorders, such as psychiatric and neurological disorders, and are also useful as anticonvulsants, for example in the treatment of epilepsy. These triazines are also non-depressant at therapeutic dose levels and are therefore advantageous as compared with depressant anti-epileptics such as phenobarbitone.

A particularly preferred compound of this type is 3,5-diamino-6-(2,3-dichlorophenyl)-1,2,4-triazine (e.g. European Patent 21121).

A known process for preparing 3,5-diamino-6-(substituted phenyl)-1,2,4-triazines, comprises reacting substituted benzoyl cyanides with aminoguanidine in aqueous solutions of strong acids such as nitric acid (J. A. Settepani and A. B. Borkovec, J. Heterocycl. Chem., 1966, 3, 188, U.S. Pat. Nos. 3,637,688; 4,486,354; 4,602,017; 4,649,139, R. W. A. Rees et al, J. Med. Chem., 1972, 15, 859; European Patent Nos. 21,121; 142,306; 247,892, Israeli Patent Nos. 60,201; 73,332; 82,710) and sulfuric acid (European Patent No. 247,892, Israeli Patent No. 82,710) to produce amidinohydrazone of the general formula (A):

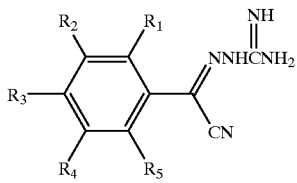

(A)

wherein $R_1$ is halogen, $C_{1-4}$ alkyl or trifluoromethyl, $R_2$ is hydrogen, halogen, $C_{1-4}$ alkyl or trifluoromethyl, or $R_1$ and $R_2$ form a —CH=CH—CH=CH— group optionally substituted by a halogen atom or a $C_{1-4}$ alkyl or trifluoromethyl group, $R_3$ and $R_4$ are independently selected from hydrogen, halogen, $C_{1-4}$ alkyl or trifluoromethyl groups and $R_5$ is hydrogen, methyl or fluorine.

3,5-Diamino-6-(substituted phenyl)-1,2,4-triazines (compounds of the general formula (B):

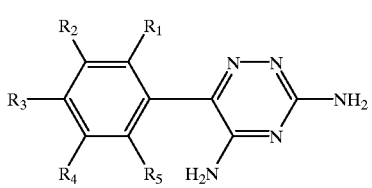

(B)

wherein $R_1$–$R_5$ are as hereinbefore defined) are obtained by ring closure of a compound of the formula A.

The ring closure is normally carried out by refluxing in an alcohol, such as methanol, ethanol, 1-propanol and the like, in the presence of a strong base, such as sodium hydroxide, potassium hydroxide and the like.

However, the reaction of substituted benzoyl cyanides with aminoguanidine in the aqueous solutions of strong acids is very slow and usually from 2 to 21 days are required to complete this reaction. On the other hand, substituted benzoyl cyanides are hydrolyzed at the reaction conditions, and overall yield of the triazines is low (from 2 to 41%) (Table).

TABLE

| Compounds of the formula (A) | Solvent of the reaction | Temperature of the reaction | Time of the reaction | Yield of the compound of the formula (B) |
|---|---|---|---|---|
| $R^6$=$R^7$=Cl $R^8$=$R^9$=$R^{10}$=H | a) DMSO and 8N aqueous nitric acid | 25° C. | 7 days | 15.6%* |
| | b) Acetonitrile and 63% aqueous sulfuric acid | 20–30° C. | 48 hours | 41%** |
| $R^6$=$R^7$=$R^9$=Cl $R^8$=$R^{10}$=H | DMSO and 8N aqueous nitric acid | 20–30° C. | 21 days | 1.6%* |
| $R^6$=$R^8$=Cl $R^7$=$R^9$=$R^{10}$=H | DMSO and 8N aqueous nitric acid | 25° C. | 24 hours | 8%*** |
| $R^7$=$R^8$=Cl $R^6$=$R^9$=$R^{10}$=H | DMSO and 8N aqueous nitric acid | 25° C. | 24 hours | 23%*** |
| $R^8$=Cl $R^6$=$R^7$=$R^9$= $R^{10}$=H | DMSO and 8N aqueous nitric acid | 25° C. | 24 hours | 37%*** |

*U.S. Pat. No. 4,486,354
**European Patent No. 247,892
***R. W. A. Rees et al, J. Med. Chem., 1972, 15, 859.

SUMMARY OF THE INVENTION

As a result of research to solve the drawbacks of the prior art methods, the present inventors have found the method for preparing the substituted benzoyl cyanide amidinohydrazones by a reaction of substituted benzoyl cyanides with aminoguanidine in a mixture of polyphosphoric acid and a solvent in the absence of water which minimizes the hydrolysis of the benzoyl cyanides.

According to the present invention substituted benzoyl cyanide amidinohydrazones can be prepared in higher yield after the reaction of substituted benzoyl cyanide with aminoguanidine in a mixture of polyphosphoric acid and acetonitrile for 24 hours.

Other objects and advantages of the present invention will be apparent from the following description.

DETAILED DESCRIPTION OF THE INVENTION

More specifically the present invention provides a process for preparing a compound of the general formula (I):

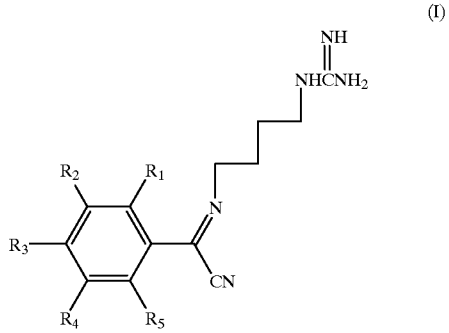

wherein $R_1$ to $R_5$ are independently selected from hydrogen, halogen, $C_{1-6}$ alkyl, $C_{2-6}$ alkenyl, $C_{2-6}$ alkynyl or $C_{1-6}$ alkoxy, all optionally substituted by one or more of halogen, hydroxy and aryl groups, as well as being independently selected from amino, mono- or disubstituted amino, alkenyloxy, acyl, acyloxy, cyano, nitro, aryl and alkylthio groups, which process comprises reacting a compound of the general formula (II):

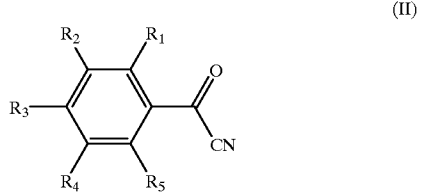

wherein $R_1$ to $R_5$ are as defined in formula (I), with aminoguanidine bicarbonate in a mixture of a water-soluble solvent and polyphosphoric acid.

Suitably the total number of carbon atoms in $R_1$ to $R_5$ is less than eight.

The phenyl ring will suitably contain up to three substituents and preferably one or two substituents.

$R_1$ to $R_5$ are preferably independently selected from halogen and hydrogen. Particularly preferred substitutions are 4 or 2,3 or 2,4 or 3,4 mono- or di- halo (especially chloro).

Preferred compounds are:

4- Chlorobenzoyl cyanide amidinohydrazone,
2,3-Dichlorobenzoyl cyanide amidinohydrazone,
2,4- Dichlorobenzoyl cyanide amidinohydrazone,
3,4- Dichlorobenzoyl cyanide amidinohydrazone.

The preparation of the compounds of the formula (II) is analogous to that described in the literature, i.e. U.S. Pat. No. 3,637,688; R. W. A. Rees et al, J. Med. Chem., 1972,15, 859.

The amount of aminoguanidine bicarbonate is preferable more than one equivalent and more preferable 1.5 molar equivalents relative to compound of the formula (II).

The amount of polyphosphoric acid is preferably from 4 to 8 g, and more preferably 5.5 g to one gram of the compound of formula (II).

The reaction solvents are preferably water-soluble solvents such as acetonitrile, tetrahydrofuran, 1,2-dimethoxyethane (monoglyme), 2-methoxyethyl ether (diglyme) and the like and more preferably acetonitrile.

The amount of the reaction solvent is preferably from 2 to 8 ml, and more preferably 5 ml to one gram of the compound of the formula (II).

The reaction temperature may be chosen from ambient temperature to the reflux temperature of the solvent, and more preferably the temperature is between 50–70° C.

Since the progress of the reaction can be monitored by using high performance liquid chromatography, the reaction may be stopped after the disappearance of the starting material.

Although amidinohydrazones of the formula (II) exist as two isomers (E-and Z-forms), for the purpose of the present invention, these compounds may exist as either of the isomers or as a mixture thereof.

After completion of the reaction, water is added to the reaction mixture to obtain a clear homogeneous mixture. The mixture is dropped to water, and a colourless precipitate is collected by filtration to obtain a wet phosphate of the compound of the formula (I).

The wet phosphate of the compound of the formula (I) is added to an aqueous alkali solution, e.g., sodium hydroxide and the like, and the mixture is stirred at ambient temperature for one hour. A precipitate is then collected by filtration, washed with water and dried at 80° C. to give a free base of the compound of the formula (I).

Triazines of the general formula (III):

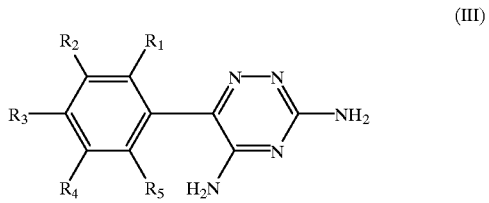

wherein $R_1$ to $R_5$ are as defined in the formula (I), can be obtained from the compound of the formula (I) by a procedure similar to that described in the literature, i.e. Beyer et al, *Chem. Ber.* 1960, 93, 2209; J. A. Settepani and A. B. Borkovec, J. Heterocycl. Chem., 1966, 3, 188, U.S. Pat. Nos. 3,637,688; R. W. A. Rees et al, *J. Med. Chem.*, 1972, 15, 859; European Patent Nos, 21,121; 247,892.

According to the present invention, the compounds of the formula (I) can be obtained in high yield from the compound of the formula (II) by using polyphosphoric acid and simple procedures.

The present invention will be concretely illustrated by Exam, which show the method for preparation of the compound of formula (I).

While the invention will now be described in connection with certain preferred embodiments in the following examples so that aspects thereof may be more fully understood and appreciated, it is not intended to limit the invention to these particular embodiments. On the contrary, it is intended to cover all alternatives modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Preparation of 2,3-Dichlorobenzoyl cyanide amidinohydrazone a) Reactor (0.5 L) was charged under nitrogen with acetonitrile (200 ml) and polyphosphoric acid (220 g), and the mixture was stirred for 0.5 hour to obtain an emulsion. Solid 2,3-dichlorobenzoyl cyanide (41 g, 0.2 mole; assay 97.5%) was added to the emulsion. Aminoguanidine bicarbonate (41 g, 0.3 mole; assay 99.0%) was added to the mixture in 5 equal portions during 2 hours at 30–40° C. The reaction mixture was stirred at 50° C. during 22 hours. Water (40 ml) was then added to the reaction mixture to obtain a clear homogeneous mixture. The mixture was dropped to water at slow stirring for 0.5 hour, and the precipitate was collected by filtration to give wet phosphate salt of 2,3-dichlorobenzoyl cyanide amidinohydrazone.

The wet phosphate salt was added at ambient temperature to 2.5% aqueous sodium hydroxide solution (500 ml), and the mixture was stirred for 0.5 hour. The precipitate was collected by filtration, washed thoroughly with water and dried at 80° C. overnight to give 43.0 g (84% yield) of 2,3-dichlorobenzoyl cyanide amidinohydrazone base.

m.p. 221–222° C. (uncorrected) (after dissolution in tetrahydrofuran, filtration of the solution and removal of the solvent to dryness in vacuo). $^1$H NMR (DMSO-d$_6$): δ (ppm)=6.7 (4H, s, NH), 7.3–7.7 (3H, m, ArH). $^{13}$C NMR (DMSO-d$_6$): δ (ppm)=113.88 and 114.53 ($\underline{C}$≡N, d, E- and Z-forms of the hydrazone), 128.24, 129.53 and 130.10 (3 $\underline{C}$—H from Ar), 163.64 [—NH—$\underline{C}$(NH$_2$)=NH]. MS (FAB): m/z 256 (MH$^+$). Analysis: Calcd. for C$_9$H$_7$Cl$_2$N$_5$: C, 42.21; H, 2.75; N, 27.35, found: C, 42.12; H, 2.77; N, 27.80.

b) The title compound was obtained in 67% yield after carrying out the reaction of 2,3-dichlorobenzoyl cyanide with aminoguanidine in a mixture of monoglyme and polyphosphoric acid.

EXAMPLE 2

Preparation of 3,5-diamino-6-(2,3-dichlorophenyl)-1,2,4-triazine a) The 2,3-dichlorobenzoyl cyanide amidinohydrazone base (43.0 g) obtained in Example 1(a) was heated under reflux in 1-propanol (560 ml) for two hours. The hot solution was filtered off, and the filtrate was cooled to 10° C. The crystals were collected by filtration, recrystallized from 1-propanol (490 ml) and dried at 100° C. to give 3,5-diamino-6-(2,3,-dichlocrophenyl)-1,2,4-triazine (34.5 g).

The 1-propanol was evaporated to dryness in vacuo from the two filtrates, and the residue was recrystallized from 1-propanol to give 4.0 g of the title compound.

Total yield (from 2,3-dichlorobenzoyl cyanide): 38.5 g (75.2%), m.p. 216–218° C. (uncorrected). $^1$H NMR (DMSO-d$_6$): δ (ppm)=6.16(2H, s, NH), 6.45 (2H, br s, NH), 7.2–7.7 (3H, m, ArH). $^{13}$C NMR (DMSO-d$_6$): δ (ppm) 129.26, 131.35 and 131.51 (3$\underline{C}$—H from Ar), 155.114 [C—$\underline{C}$(NH$_2$)=N—], 162.95 [=N—$\underline{C}$(NH$_2$)=N—]. MS (FAB): m/z 256 (MH$^+$).

b) Wet phosphate obtain ed by the procedure similar to that of Example 1(a) from 200 g (0.959 mole; assay: 95.91%) of 2,3-dichlorobenzoyl cyanide was added to 1-propanol (2.0 L), and the mixture was heated to 65° C. at stirring. 45% Aqueous sodium hydroxide solution (185 ml) was then added to this mixture to produce pH 10, and the mixture was heated under reflux for two hours. The water phase was collected, and the organic phase was cooled to 10° C. The colourless crystals were collected by filtration, recrystallized from 1-propanol (2.0 L) (the hot solution was filtered) and dried at 100° C. to give 160 g of the title compound. An additional 20.0 g of the title compound was obtained from the filtrates. Total yield (from 2,3-dichlorobenzoyl cyanide): 180 g (73.3%).

c) The title compound was obtained in 60% total yield (from 2,3-dichilorobenzoyl cyanide) from 2,3-dichlorobenzoyl cyanide amidinohydrazone obtained in Example 1(b).

EXAMPLE 3

Preparation of 2,4-dichlorobenzoyl cyanide amidinohydrazone

The title compound was prepared as in Example 1(a). Yield: 65% $^1$H NMR (DMSO-d$_6$): δ (ppm)=6.70 (4H, s, NH), 7.4–7.8 (3H, m, ArH). $^{13}$C NMR (DMSO-d$_6$): δ (ppm)=114.16 and 114.65 ($\underline{C}$≡N, d, E- and Z-forms of the hydrazone), 128.06, 130.05 and 132.22 (3 $\underline{C}$—H from Ar), 163.87 [—NH—$\underline{C}$(NH$_2$)=NH]. MS (FAB): m/z 256 (MH$^+$)

EXAMPLE 4

Preparation of 3,5-Diamino-6-(2,4-dichlorophenyl)-1,2,4-triazine

The title compound was prepared as in Example 2(a) from 2,4-dichlorobenzoyl cyanide amidinohydrazone obtained in Example 3. The solvent for ring closure was a mixture of 1-propanol and dimethylsulfoxide (5:1). Total yield (from 2,4-dichlorobenzoyl cyanide): 55%; m.p. 220–222° C. (uncorrected).

$^1$H NMR (DMSO-d$_6$): δ (ppm)=6.40 (2H, s, NH), 6.66 (2H, br s, NH), 7.1–7.8 (3H, m, ArH). $^{13}$C NMR (DMSO-d$_6$): δ (ppm)=127.60, 129.04 and 133.19 (3 $\underline{C}$—H from Ar), 154.21 [C—$\underline{C}$(NH$_2$)=N—], 161.98 [=N—$\underline{C}$(NH$_2$)=N—]. MS (FAB): m/z 256 (MH$^+$).

EXAMPLE 5

Preparation of 3,4-Dichlrobenzoyl cyanide amidinohydrazone

The title compound was prepared as in Example 1(a). Yield: 86%. $^1$H NMR (DMSO-d$_6$): δ (ppm)=7.28 (4H, s, NH), 7.5–8.3 (3H, m, ArH). $^{13}$C NMR (DMSO-d$_6$): δ (ppm)=112.44 and 117.20 ($\underline{C}$≡N, d, E- and Z-forms of the hydrazone), 125.20, 126.06 and 131.95 (3 $\underline{C}$—H from Ar), 160.99 [—NH—$\underline{C}$(NH$_2$)=NH]. MS (FAB): m/z 256 (MH$^+$).

EXAMPLE 6

Preparation of 3,5-Diamino-6-(3,4-dichlorophenyl)-1,2,4-triazine

The title compound was prepared as in Example 2(a) from 3,4-dichlorobenzoyl cyanide amidinohydrazone obtained in Example 5. The solvent for the ring closure was a mixture of 1-propanol and dimethyl sulfoxide (11). Total yield (from 3,4-dichlorobenzoyl cyanide): 76%; m.p. 222–224° C. (uncorrected).

$^{13}$C NMR (DMSO-$d_6$): δ (ppm)=128.6, 130.24 and 130.83 (3 C—H from Ar), 155.02 [C—C(NH$_2$)=N—], 158.99 [=N—C(NH$_2$)=N—]. MS (FAB): m/z 256 (MH$^+$).

EXAMPLE 7

Preparation of 4-Chlorobenzoyl cyanide amidinohydrazone

The title compound was prepared as in Example 1(a). Yield: 80%. $^1$H NMR (DMSO-$d_6$): δ (ppm)=6.70 (4H, s, NH), 7.2–8.0 (4H, m, ArH). $^{13}$C NMR (DMSO-$d_6$): δ (ppm)=113.49 and 116.79 (C≡N, d, E- and Z-forms of the hydrazone), 125.95 and 128.44 (4 C—H from Ar), 163.90 [—NH—C(NH$_2$)=NH]. MS (FAB): m/z 222 (MH$^+$).

EXAMPLE 8

Preparation of 3,5-Diamino-6-(4-chlorophenyl)-1,2, 4-triazine

The title compound was prepared as in Example 2(a) from 4-chlorobenzoyl cyanide amidinohydrazone obtained in Example 7. The solvent for the ring closure was a mixture of 1-propanol and dimethyl sulfoxide (4:1). Total yield (from 4-chlorobenzoyl cyanide): 72%; m.p. 219–221° C. (uncorrected).

$^1$H NMR (DMSO-d6): δ (p)=6.43 (2H, s, NH), 6.73 (2H, br s , NH), 7.3–7.7 (4H, m, ArH). $^{13}$C NMR (DMSO-$d_6$): δ (ppm)=128.69 and 129.87 (4 C—H from Ar), 154.32 [C—C(NH$_2$)=N—], 1,161.55 [=N—C(NH$_2$)=N—]. MS (FAB): m/z 222 (MH$^+$).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims aretherintended to be embraced ther.

What is claimed is:

1. A process for preparing a compound of the general formula (I):

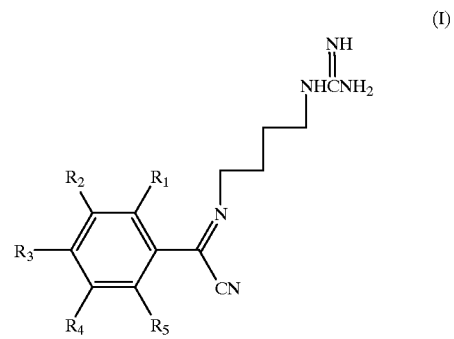

wherein
$R_1$ to $R_5$ are independently selected from hydrogen, halogen, $C_{1-6}$ alkyl, $C_{2-6}$ alkenyl, $C_{2-6}$ alkynyl or $C_{1-6}$ alkoxy, all optionally substituted by one or more of halogen, hydroxy and aryl groups, as well as being independently selected from amino, mono- or disubstituted amino, alkenyloxy, acyl, acyloxy, cyano, nitro, aryl and alkylthio groups, which process comprises reacting a compound of the general formula (II):

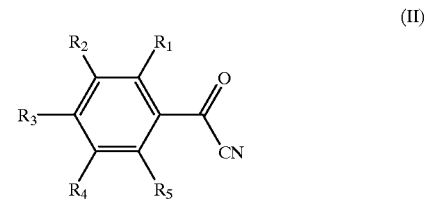

wherein
$R_1$ to $R_5$ are as defined in formula (I), with aminoguanidine bicarbonate in a mixture of a water-soluble solvent and polyphosphoric acid.

2. A process according to claim 1 wherein the amount of aminoguanidine bicarbonate is more than 1 equivalent per 1 equivalent of the compound of formula (II).

3. A process according to claim 1 wherein the amount of polyphosphoric acid is from 4 to 8 g per one gram of the compound of formula (II).

4. A process according to claim 1 wherein said water-soluble solvent is acetonitrile.

5. A process according to claim 1 wherein the reaction of the compound of formula (II) with aminoguanidine bicarbonate is carried out at a temperature of about 25–150°C.

6. A process according to claim 1 wherein the compound of formula (I) is 2,3-Dichlorobenzoyl cyanide amidinohydrazone.

* * * * *

UNITED STATES PATENT AND TRADEMARK OFFICE
CERTIFICATE OF CORRECTION

PATENT NO.      : 6,329,521 B2
DATED           : December 11, 2001
INVENTOR(S)     : Joseph Kaspi et al.

It is certified that error appears in the above-identified patent and that said Letters Patent is hereby corrected as shown below:

Title page,
Item [75], "Nadaka" has been replaced with -- Naddaka --.
Item [75], "Lexmer" has been replaced with -- Lexner --.

Item[57], ABSTRACT, the first chemical structure, formula (I), has been replaced with

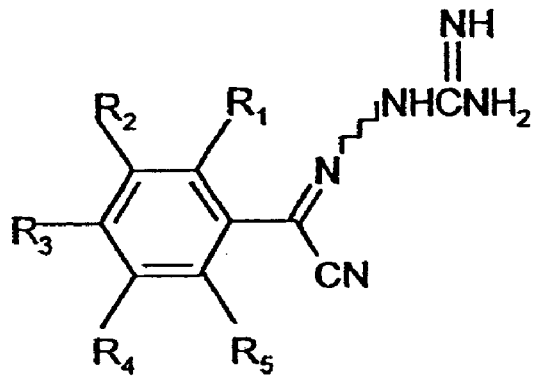

Column 3,
Line 5, the chemical structure, formula (I), has been replaced with

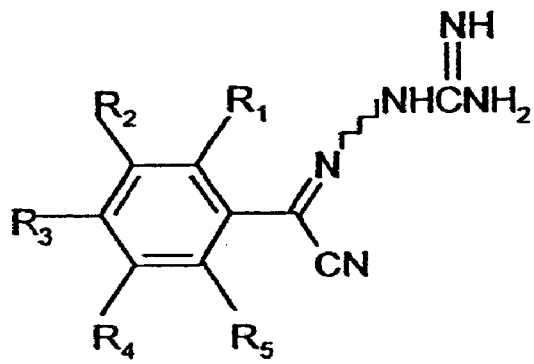

UNITED STATES PATENT AND TRADEMARK OFFICE
CERTIFICATE OF CORRECTION

PATENT NO.    : 6,329,521 B2
DATED         : December 11, 2001
INVENTOR(S)   : Joseph Kaspi et al.

It is certified that error appears in the above-identified patent and that said Letters Patent is hereby corrected as shown below:

Column 8,
Line 5, the chemical structure, formula (I), has been replaced with

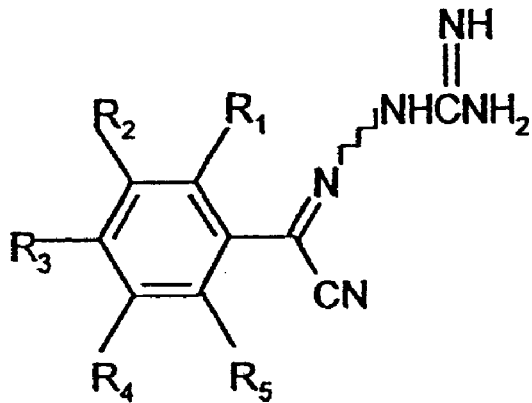

Signed and Sealed this

Twentieth Day of August, 2002

*Attest:*

*Attesting Officer*

JAMES E. ROGAN
*Director of the United States Patent and Trademark Office*